(12) United States Patent
McNew

(10) Patent No.: US 7,108,654 B2
(45) Date of Patent: *Sep. 19, 2006

(54) METHOD AND APPARATUS FOR APPLYING FREQUENCY VIBRATIONS THERAPEUTICALLY

(76) Inventor: Barry McNew, 1288 Palisade Dr., Cottonwood, AZ (US) 86326

(*) Notice: Subject to any disclaimer, the term of this patent is extended or adjusted under 35 U.S.C. 154(b) by 122 days.

This patent is subject to a terminal disclaimer.

(21) Appl. No.: 10/408,537

(22) Filed: Apr. 7, 2003

(65) Prior Publication Data

US 2003/0191359 A1    Oct. 9, 2003

Related U.S. Application Data

(63) Continuation of application No. 09/359,819, filed on Jul. 23, 1999, now Pat. No. 6,544,165.

(51) Int. Cl.
*A61M 21/00* (2006.01)
(52) U.S. Cl. ..................................................... 600/28
(58) Field of Classification Search ............ 600/26–28, 600/300; 128/897, 898; 607/1, 88, 90, 91
See application file for complete search history.

(56) References Cited

U.S. PATENT DOCUMENTS

| | | | | |
|---|---|---|---|---|
| 1,935,294 A | * | 11/1933 | Jacquelet et al. | 315/344 |
| 3,014,477 A | * | 12/1961 | Carlin | 600/27 |
| 3,085,568 A | * | 4/1963 | Whitesell | 601/55 |
| 3,826,250 A | * | 7/1974 | Adams | 601/16 |
| 4,507,816 A | * | 4/1985 | Smith, Jr. | 5/666 |
| 5,266,070 A | * | 11/1993 | Hagiwara et al. | 600/27 |
| 5,318,503 A | * | 6/1994 | Lord | 600/27 |
| 5,577,990 A | * | 11/1996 | Widjaja et al. | 600/27 |
| 5,645,578 A | * | 7/1997 | Daffer et al. | 607/91 |
| 5,865,771 A | * | 2/1999 | Shuto et al. | 601/47 |
| 6,544,165 B1 | * | 4/2003 | McNew | 600/27 |

* cited by examiner

*Primary Examiner*—Samuel G. Gilbert
(74) *Attorney, Agent, or Firm*—Kunzler&Associates

(57) ABSTRACT

This invention relates to a method and apparatus for applying Frequency Vibrations of Sound and Light (hereinafter sometimes referred to as "FVSL") to a user for the administration of therapeutic treatment including relaxation and other benefits.

23 Claims, 2 Drawing Sheets

METHOD AND APPARATUS FOR APPLYING FREQUENCY VIBRATIONS THERAPEUTICALLY

This Application is a continuation application of U.S. patent application Ser. No. 09/359,819, filed on Jul. 23, 1999, now U.S. Pat. No. 6,544,165, and entitled "Method and Apparatus for Applying Frequency Vibrations Therapeutically".

FIELD OF THE INVENTION

This invention relates to a method and apparatus for applying Frequency Vibrations of Sound and Light (hereinafter sometimes referred to as "FVSL") to a user for the administration of therapeutic treatment including relaxation and other benefits.

BACKGROUND OF THE INVENTION

The therapeutic benefits of utilizing light, sound, color, smell, magnetic fields and vibration are known. Medical evidence indicates that the health of people may be affected by exposure to light. For example, a condition known as Seasonal Affective Disorder occurs during seasonal periods of low light and is characterized by a depressed condition in those people so affected.

It is also known that sound plays a substantial role in changes of pulse frequency, blood pressure, blood circulation, muscle relaxation, perspiration and oxygen consumption of a person. Previously, sound therapy has been applied to a user's ears and body, light has been applied to a user's eyes, and other stimuli have been combined to relax a user. Further, it is well known that the different parts of the human brain are known to correspond to different parts of the body; for example, the two hemispheres of the brain are known to correspond to different sides of the body. It would be advantageous over the prior art to stimulate the user's brain through the application of sound specifically and independently directed to the right and left sides of the user's body along with the application of the sound to the user's ears and light to the user's eyes.

The object of the present invention is to provide better stimulation to a user's mind and body using acoustic vibrations, also known as sound, directed to the right and left sides of the human body and to provide a substantially dark space to the user's eyes which includes at least one light source for controlling light to the user's eyes. Certain forms of the enclosure can also act as a sound reflector to direct acoustic vibrations to the skin and ears of the user.

The present invention relates to a method and an apparatus for applying Frequency Vibrations of Sound and Light to a user's body and eyes to facilitate physiological and psychological benefits to the user such as relaxation, and especially the application of acoustic vibrations from separate transducers to the right and left side of a user's body.

SUMMARY OF THE INVENTION

In accordance with this invention, a method and apparatus for applying Frequency Vibrations of Sound and Light to a user using a therapeutic light and sound system are disclosed.

The therapeutic light and sound system comprises a support structure having a longitudinal centerline, a top side, and a bottom side for supporting a user; at least two transducers arranged on opposite sides of the longitudinal centerline for producing acoustical vibrations substantially directed to the right side and left side of the user, respectively; an enclosure module for forming a substantially dark space for the user's eyes, and at least one light source coupled to the substantially dark space for transmitting light to the user's eyes. Preferably, the therapeutic light and sound system further comprise a mat placed on the top side of the support structure for cushioning the user and transmitting the acoustical waves to the right side and left side of the user's body. The invention may also include a sound generator for actuating the transducers.

Another aspect of the invention relates to a therapeutic light and sound system comprising a support structure including: a top side for supporting a user, the user having a right side and a left side; at least one right transducer arranged on the support structure for transmitting acoustic vibrations to the right side of the user; at least one left transducer arranged on the support structure for transmitting acoustic vibrations to the left side of the user; an enclosure module for forming a substantially dark space for the user's eyes; and at least one selectively energized light source coupled to the substantially dark space for transmitting light to the user's eyes.

The method of therapeutic treatment using light and sound comprises the steps of: supporting a user on a support structure having a top side and including at least one right transducer arranged below the user's body corresponding to the user's right side and having at least one left transducer arranged below the user's body corresponding to the user's left side; transmitting acoustical vibrations from right transducers substantially to the right side of the user's body and transmitting acoustical vibrations from the left transducers substantially to the left side of the user's body; providing an enclosure module for forming a substantially dark space for the user's eyes; and coupling at least one selectively energized light source to the substantially dark space for transmitting light to user's eyes.

DESCRIPTION OF THE DRAWINGS

The invention will be more readily understood from a non-limiting description of a preferred embodiment that follows and from the diagrammatic figure of the drawings.

In the drawings.

DESCRIPTION OF THE PREFERRED EMBODIMENTS

Figure 1:
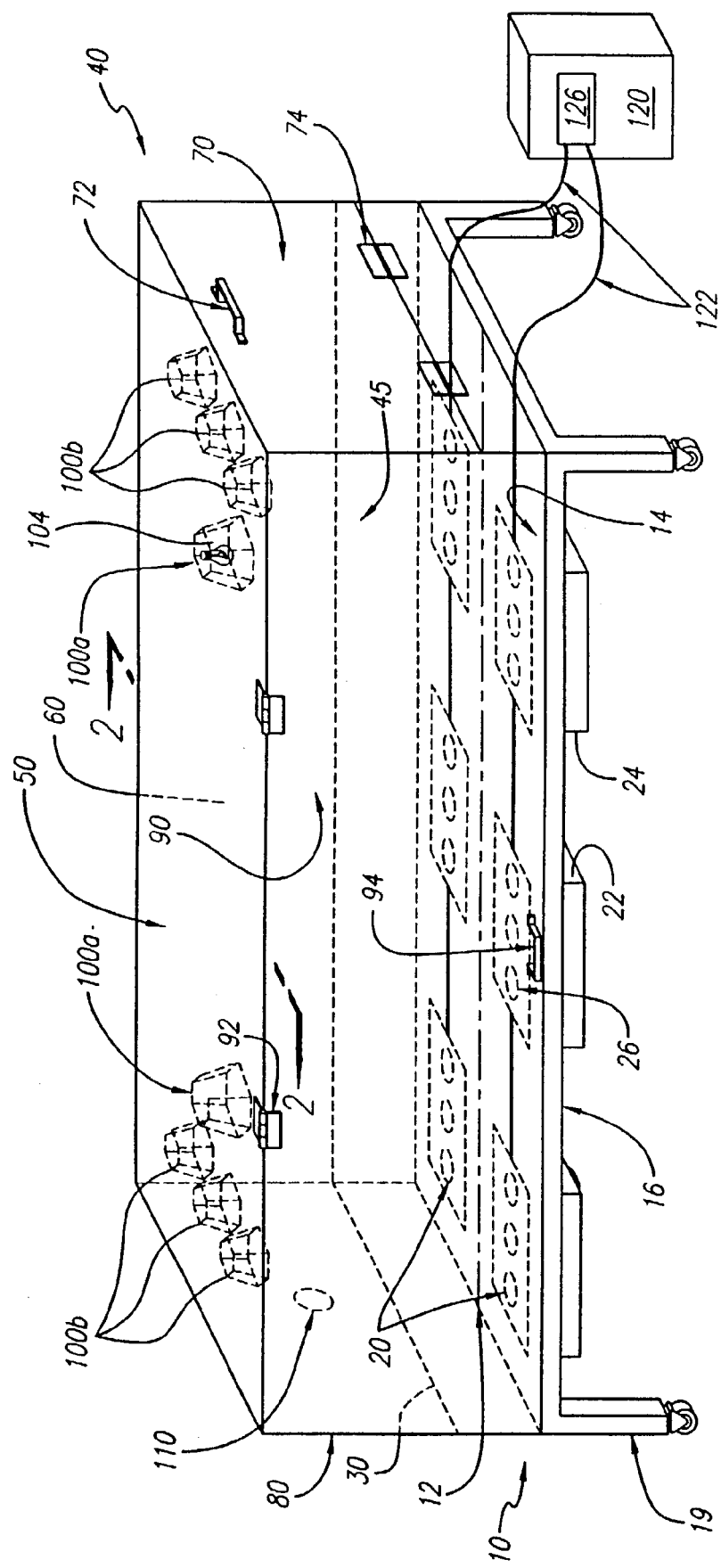
FIG. 1 is a non-limiting diagram illustrating the system in a preferred embodiment of the present invention.

Referring now to FIG. 1, there is shown a schematic diagram for one embodiment of the present invention. As shown in FIG. 1, the embodiment of the therapeutic light and sound system has a support 10 comprising a longitudinal centerline 12, a top side 14, and a bottom side 16. The support 10 should be large enough to support the user and of sufficient strength to remain substantially rigid when subjected to the user's weight. Examples of materials that can be used for the support include, but are not limited to, wood, sound board, plywood, particle board, composite insulation board, plastic, glass, Plexiglas, fiberglass, metal, stone, marble, etc. Preferably the support material would provide a sound insulation or a sound insulating material that could be attached to the support material. Also, the supporting material would preferably be substantially opaque to light transmission or could be covered with a light absorbing material. For example, the supporting material could be substantially opaque, painted or covered with a light absorbing material.

In a preferred embodiment of the present invention, the support 10 includes at least one supporting member 19. For example, the supporting member may be a single solid base or column. In a more preferred embodiment of the present invention, the support 10 includes at least two supporting members. In a most preferred embodiment of the present invention, the support 10 includes at least four supporting members. For example, FIG. 1 shows the best mode including four supporting members 19 on movable wheels.

The support 10 further includes at least two transducers 20 arranged on opposite sides of the longitudinal centerline 12. The longitudinal centerline as defined for the purposes of this invention corresponds to the right and left sides of a user which may or may not correspond to the exact centerline of support. The transducers corresponding to the right side of the user are also known as the right transducers and the transducers corresponding to the left side of the user are also known as the left transducers.

Each transducer emits acoustic vibrations about the range of human auditory response. Light and sound vibrations can be defined by either the frequency or wavelength. Preferably the sound frequency range produced is from about 10 Hz to about 25,000 Hz, and more preferably sound frequency is from about 30 Hz to about 20,000 Hz. The transducers are also known as speakers. For example, individual speakers may be full range speakers or may produce frequencies of a limited range. The transducers are preferably electro-mechanical in nature. Limited range speakers are sometimes referred to as sub-woofers, woofers, mid-range and tweeters.

The transducers 20 on the opposite sides of the longitudinal centerline 12 are preferably separated by an attenuating barrier 22 placed between the transducers. The transducers may be placed in groups or placed individually. Preferably, at least one attenuating barrier is provided to reduce transmission of acoustical waves between the transducers on opposite sides of the longitudinal centerline. More preferably, attenuating barriers are also placed between groups of or between individual transducers on the same side. Most preferably, an attenuating housing 24 can be formed by fully enclosing the transducers, either in groups or individually, by using attenuating barriers 22. For example, FIG. 1 shows eighteen transducers 20 grouped in six sets of three attached to the bottom side of the support 10. The groups of three transducers 20 are separated by attenuating barriers 22 which, in the disclosed embodiment, form attenuating housings 24.

The transducers 20 may be placed either above, below or mounted within the support 10. preferably, the transducers 20 are attached to the support 10. The transducers 20 may be either attached to the top side 14, the bottom side 16 or set within the body of the support. If the transducers 20 are attached to the bottom of the support, then an acoustical transmitter 26 must be used if the support does not substantially transmit the acoustic vibrations. Such an acoustical transmitter; for example, may be a plurality of holes in the support, a single opening in the support, or some frequency transmitting material in the support corresponding to the transducers.

One example of the acoustical transmitter 26 may be an opening or holes that correspond to the removal of material in any shape and extending from the bottom side 16 of the support to the to side 14 of the support that allow for the transmission of the acoustic vibrations. For example the openings or holes may remove material in the shapes of cubes, parallel pipeds, spheres, pyramids, cones, cylinders, etc. Preferably, the opening or holes are cylindrically shaped. A second type of acoustical transmitter may be a frequency transmitting material that may replace the opening or holes to allow for the transmission of the acoustic vibrations.

An enclosure module is required to create a substantially dark space at least around the user's eyes. In the preferred embodiment shown in FIG. 1, an enclosure module 40, of any suitable shape, with the top side 16 of the support 10 acting as the base, forms a substantially dark space 45 such that the substantially dark space 45 is sufficiently large enough to accommodate a user. In one preferred embodiment of the present invention, the enclosure module 40 would provide some sound insulation, or some sound insulating material could be attached to the inside or outside of the enclosure module 40. In another preferred embodiment of the present invention, the enclosure module 40 could be covered with a light absorbing material, and more preferably, the enclosure module 40 would be substantially opaque to light transmission. For example, the enclosure module 40 could be substantially opaque, or painted or covered with a light absorbing material. In another embodiment of the present invention, the enclosure module 40 may be of any size but preferably the substantially dark space 45 is of sufficient size to enclose the user. Examples of enclosure modules that can form a substantially dark space include light excluding eye goggles or rooms from which light can be substantially excluded.

In FIG. 1, the enclosure module 40 is made of wood and has a top 50, a back 60, a first 70, a second side 80, and a front 90. Access to the interior of the substantially dark space 45, shown in FIG. 1, is through at least one access port. For example, in FIG. 1 the front 90 and the top 50 are connected with hinges 92 that allow the front 90 to be pivotally lifted using handle 94 thereby forming an access port for the user. Other access ports may be created in the enclosure module 40, the support 10, or in combination of the enclosure module 40 and support 10. Optionally, a communication system is available so the user may communicate with a person outside the system.

In the preferred embodiment of the present invention shown in FIG. 1, a second access port in the first side 70 having hinges 74 and a handle 72 is shown. The second access port shown in FIG. 1 may also be used to communicate with the user while maintaining the substantially dark space (i.e., a communication system) by opening the second access port slightly. Other examples of mechanical and electrical methods of communication systems are available, such as two-way intercoms, etc.

The substantially dark space 45 includes at least one selectively energized light source 100. The light source or sources may be any sort of illuminating device including, but not limited to, incandescent bulbs, fluorescent lights or display terminals or combinations thereof. The light source 100 may be a white light source to simulate sunlight. Alternatively, the light source or sources may produce colored light by the light source itself or by using a color filter. FIG. 1 shows eight light sources 100*a* and 100*b* attached to the top 50. Preferably, the lights are enclosed in a multiple-sided mirrored reflector where the number of sides is at least equal to two. In the preferred embodiment of the present invention shown in FIG. 1, two of the light sources, 100*a*, are white light enclosed in a six-sided mirrored reflector 104 and six other light sources 100*b* use colored filters or colored lights. The light sources produce light that is visible to the user's eye including, but not limited to, red, orange, yellow, violet, blue and green. The wavelengths of the light are generally between 400 nanometers and 800 nanometers. The light source, or light sources, are coupled to the substantially dark space 45 by placing the light source, or light sources, anywhere within the substantially dark space or the light may be transmitted by transmitting light into the substantially dark space 45 by some method, such as, for example, a fiber optic. Preferably, the light source, or sources, 100 are mounted on the enclosure module 40 in a way that light reaches the substantially dark space 45. More preferably, the light sources are mounted above the user. Further, the light source, or light sources, may be controlled individually or in groups by actuating switches. Preferably, the actuating switch can vary the intensity and duration of the selectively energized light or light sources. More preferably, each light source has a separate actuating switch for varying the light source intensity.

The substantially dark space 45 may also have a temperature moderation device 110. Such temperature moderation devices include, but are not limited to, for example, a fan, a heater and an air conditioner. The temperature moderation device may also provide ventilation for the user. FIG. 1 shows a hole 110 inserted in the second side 80 which can accommodate a fan as a temperature moderation device. Such devices could be mounted or equipped with light baffles to prevent unnecessary light from entering the substantially dark space 45.

The present invention also includes at least one sound generator 120 having at least two outputs 122 that are connected to the transducers 20. The sound generator 120 may be any sort of device that generates an electrical output which may be converted into acoustic vibrations. Examples of some types of sound generators include, but are not limited to, stereo systems, radio receivers, phonographs, compact disc players, tape recorders and players, cable box decoders, satellite signal capturing devices, televisions, video cassette recorders, Internet connecting devices, etc. The sound generator 120 includes either an internal or external amplifier to actuate the transducers. For example, FIG. 1 shows a stereo system 120 including an external amplifier 126. The sound generator 120 may be placed anywhere, but in one preferred embodiment of the present invention, the sound generator 120 may be placed on the top 50 of the enclosure module 40 and a covering unit may be made to cover the sound generator 120.

Figure 2:
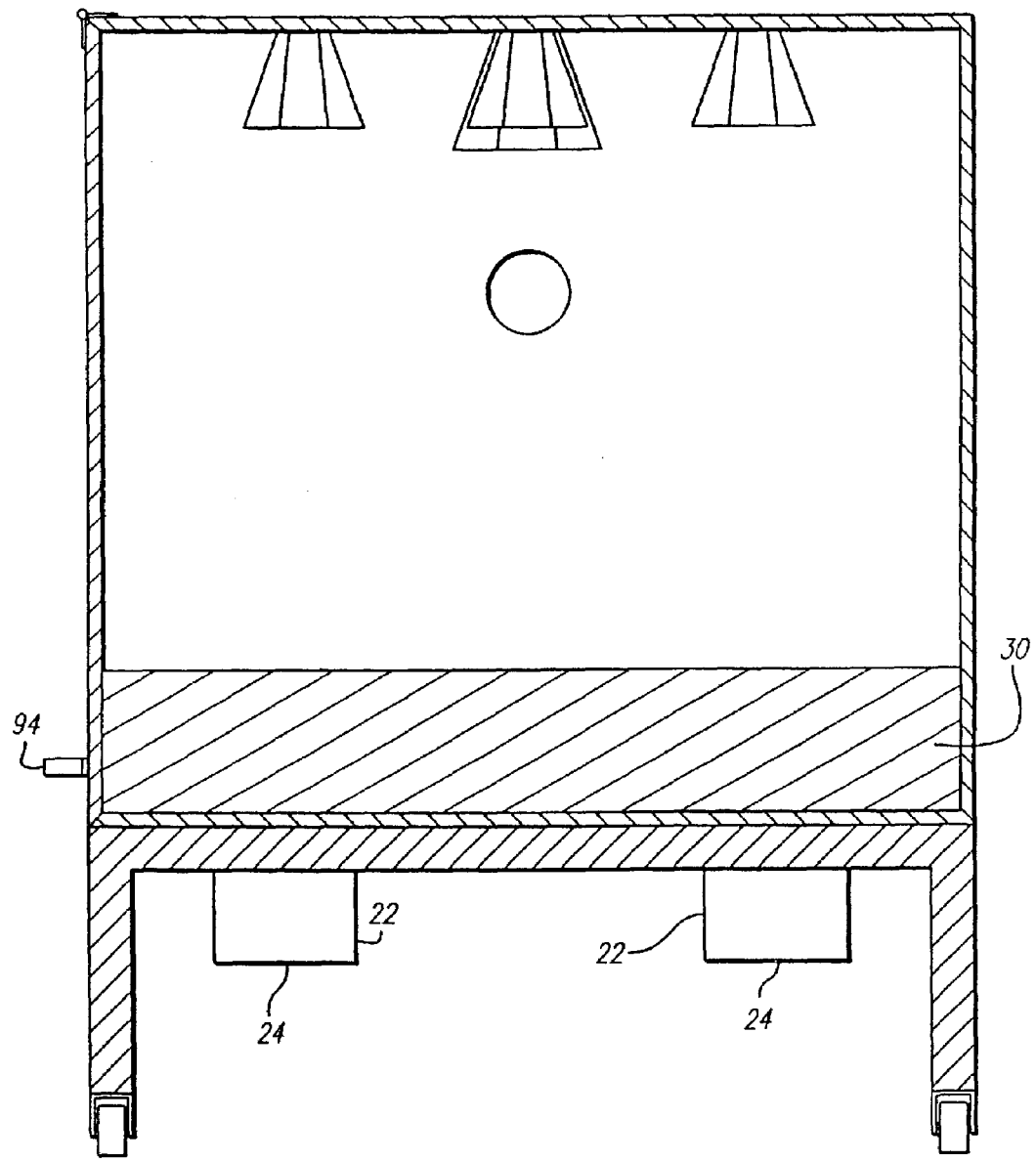
FIG. 2 is a non-limiting diagram showing a cross-sectional view in a preferred embodiment of the present invention.

Referring to FIG. 2, the acoustic vibrations produced by each of the transducers are directed upward through a mat 30 towards either the right side or left side of a user. The mat 30 may be of any porous material which allows the frequency vibrations to reach the user. Examples of some types of material that the mat may be composed of include, but are not limited to, polyethylene foam, sponge, cotton, and other foam rubbers and plastics, etc. The mat 30 may also have a covering that does not substantially reduce the frequency vibrations. The mat provides a cushion on which the user may lay on either the user's front or the user's back with the midline of the body of the user substantially between the right and left transducers.

Controls for the sound generator and the actuating switches may be accessible to the user or may be controlled outside the substantially dark space 45. Preferably, the right transducer, or transducers, and the left transducer, or transducers, may be proportionally controlled. An example of proportional control is balance between the right transducer, or transducers, and the left transducer or transducers. More preferably, the right transducer, or transducers, as a set, and the left transducer, or transducers, as a set, may be controlled using separate controls. Most preferably, each transducer may be controlled using a separate control. In another preferred embodiment of the present invention using controls, the lights may be selectively energized for duration and light intensity by an actuating switch.

The present invention may also employ a controller to control the sound generator or generators, one or more light sources, or both. The controller may be either a specifically designed device or a general purpose computer employing a software program to control delivery of the frequency vibrations to the user. In another preferred embodiment of the present invention, the controller may control any combination of the lights or the right and left transducers. The lights and the right and left transducers may also be controlled in a related manner such that the acoustic vibrations and light are coordinated to stimulate the user's brain.

Further, the present invention may also incorporate an aroma device to simulate the olfactory of the user (also known as the nose).

Whereas, a specific preferred embodiment of the present invention has been described, it will be understood that variations and modifications may be made without departure from the spirit and scope of the present invention as set forth in the appended claims.

What is claimed is:

1. A therapeutic light and sound system comprising:
   a support structure for supporting a user, said support structure having a longitudinal centerline;
   a first set of transducers configured to produce acoustic vibrations, the first set of transducers located on the support structure wholly on a first side of the longitudinal centerline and beneath the user, the location of the first set of transducers being configured to allow the acoustic vibrations to travel substantially directly through air from the first set of transducers to a first side of the user;
   at least one light source, said at least one light source comprising visible light; and
   one or more controllers for adjusting the first set of transducers and the light source in a manner such that the acoustic vibrations and light are coordinated to therapeutically stimulate said user.

2. The therapeutic light and sound system according to claim 1 further comprising an enclosure disposed around at least part of the user, the enclosure comprising a light-absorbent material.

3. The therapeutic light and sound system according to claim 1, wherein said at least one transducer operates between about 10 Hz and 25,000 Hz.

4. The therapeutic light and sound system according to claim 3, wherein said first set of transducers operates between about 30 Hz and 20,000 Hz.

5. The therapeutic light and sound system according to claim 1, wherein said at least one light source comprises at least one light source selected from the group consisting of an incandescent bulb, a fluorescent light, a display terminal and combinations thereof.

6. The therapeutic light and sound system according to claim 1, wherein said at least one light source comprises simulated sunlight.

7. The therapeutic light and sound system according to claim 1, further comprising a color filter which functions in conjunction with said at least one light source.

8. The therapeutic light and sound system according to claim 1, wherein said at least one light source delivers light to said user in a range of from about 400 nanometers to about 800 nanometers.

9. The therapeutic light and sound system according to claim 1, wherein said at least one light source is separately controlled by at least one actuating switch which separately controls at least intensity of the light source.

10. The therapeutic light and sound system according to claim 1, further comprising an attenuating barrier disposed on the support structure, the attenuating barrier configured to substantially restrict the acoustic vibrations to one side of the longitudinal centerline.

11. The therapeutic light and sound system according to claim 1, further comprising a second set of transducers configured to produce acoustic vibrations, the second set of transducers located beneath the user on the support structure on a second side of the longitudinal centerline across from the first set of transducers, the location of the second set of transducers being configured to allow the acoustic vibrations to travel substantially directly from the second set of transducers to a second side of the user.

12. The therapeutic light and sound system according to claim 1, further comprising a mat disposed between the support structure and the user, the mat comprising a porous material configured to allow the acoustic vibrations to reach the user.

13. The therapeutic light and sound system according to claim 1, further comprising a multiple-sided reflector disposed immediately around said at least one light source, the reflector configured to deliver reflected light to the user.

14. The therapeutic light and sound system according to claim 1, wherein said at least one light source comprises multiple light sources, each light source including a corresponding multiple-sided reflector configured to deliver reflected light to the user, a certain number of the light sources configured to deliver white light, and the remaining number of the light sources configured to deliver colored light.

15. A method of therapeutic treatment of a user having first and second sides using light and sound, the user supported on a support comprising the steps of:
  directing a first set of acoustical vibrations from a first set of transducers connected to the support substantially directly through air toward the first side of the user's body;
  directing visible light toward the user's eyes; and
  adjusting the light and the acoustical vibrations such that the acoustical vibrations and light are coordinated to therapeutically stimulate said user.

16. The method of therapeutic treatment of claim 15, further comprising directing a second set of acoustical vibrations from a second set of transducers connected to the support substantially directly through air toward only the second side of the user's body.

17. The method of therapeutic treatment of claim 15, wherein the light originates from a light source, and further comprising reflecting the light immediately after the light leaves the light source and directing the reflected light onto the user.

18. A therapeutic light and sound system comprising:
  a support structure comprising a longitudinal centerline and a top side for supporting a user having a fight side and a left side;
  at least one fight transducer arranged on the support structure for transmitting acoustic vibrations substantially directly through air to the right side of the user;
  at least one left transducer arranged on the support structure for transmitting acoustic vibrations substantially directly through air to the left side of the user;
  an enclosure module coupled to at least one light source comprising visible light; and
  a controller configured to adjust the acoustic vibrations transducers and the light source in a manner such that the acoustic vibrations and light are coordinated to therapeutically stimulate said user.

19. The therapeutic light and sound system according to claim 18, wherein said enclosure module comprises a light-absorbent material and forms a substantially dark space for at least one eye of the user.

20. The therapeutic light and sound system according to claim 16, wherein said at least two transducers operate between about 10 Hz and 25,000 Hz.

21. The therapeutic light and sound system according to claim 18, wherein each said at least one light source is separately controlled by at least one actuating switch which separately controls at least intensity of each light source.

22. The therapeutic light and sound system of claim 18, wherein the controller is configured to proportionately adjust the transducers.

23. The therapeutic light and sound system of claim 16, wherein the at least one right transducer comprises three sets of transducers disposed longitudinally along the right side of the user, each set approximately corresponding to a third of the user's length, and wherein the at least one left transducer comprises three sets of transducers disposed longitudinally along the left side of the user, each set approximately corresponding to a third of the user's length, and wherein the controller is configured to proportionately adjust the transducers between the right and left transducers and between the transducers disposed longitudinally the right or left sides of the user.

* * * * *

UNITED STATES PATENT AND TRADEMARK OFFICE
CERTIFICATE OF CORRECTION

| | |
|---|---|
| PATENT NO. | : 7,108,654 B2 |
| APPLICATION NO. | : 10/408537 |
| DATED | : September 19, 2006 |
| INVENTOR(S) | : Barry McNew |

It is certified that error appears in the above-identified patent and that said Letters Patent is hereby corrected as shown below:

Column 8
  Line 31, "claim 16 wherein" should read --claim 18 wherein--.

Column 8
  Line 39, "of claim 16" should read --of claim 18--

Signed and Sealed this

Seventeenth Day of April, 2007

JON W. DUDAS
*Director of the United States Patent and Trademark Office*